United States Patent [19]

Miyauchi et al.

[11] Patent Number: 5,514,715
[45] Date of Patent: *May 7, 1996

[54] NEW ANTIMICROBIAL AGENT, FR109615 AND PRODUCTION THEREOF

[75] Inventors: Michiyo Miyauchi; Eisaku Tsujii; Masami Ezaki; Seiji Hashimoto; Masakuni Okuhara, all of Tsukuba, Japan

[73] Assignee: Fujisawa Pharmaceutical Co., Ltd., Osaka, Japan

[*] Notice: The term of this patent shall not extend beyond the expiration date of Pat. No. 5,037,809.

[21] Appl. No.: 391,469

[22] Filed: Feb. 21, 1995

Related U.S. Application Data

[63] Continuation of Ser. No. 258,363, Jun. 10, 1994, abandoned, which is a continuation of Ser. No. 133,928, Oct. 12, 1993, abandoned, which is a continuation of Ser. No. 888,443, May 28, 1992, abandoned, which is a continuation of Ser. No. 655,996, Feb. 15, 1991, abandoned, which is a continuation of Ser. No. 471,039, Jan. 26, 1990, Pat. No. 5,037,809, which is a continuation of Ser. No. 215,339, Jul. 5, 1988, abandoned.

[30] Foreign Application Priority Data

Jul. 10, 1987 [GB] United Kingdom ............... 8716278

[51] Int. Cl.$^6$ .................................................. A61K 31/195
[52] U.S. Cl. .................................................. 514/561
[58] Field of Search .................... 514/530, 561; 562/504

[56] References Cited

U.S. PATENT DOCUMENTS 5,037,809  8/1991  Miyauchi ............................. 514/561

FOREIGN PATENT DOCUMENTS 139439   5/1985  European Pat. Off. .
2624290  4/1977  Germany .
63-30044 4/1988  Japan .

OTHER PUBLICATIONS

Polvech, Bull. Soc. Chim., Fr., (9–10, PT2) pp. 995–998 (1977).
Segal, Br. J. Pharmac., 54, pp. 181–188 (1975).
Goto, Chem. Abstr., 94:1855k (1981).
Goto, Nucleic Acids Symp. Ser., 8, pp. s73–s74 (1981).
Roberts, "Basic Principles of Organic Chemistry," pp. 599–603 (1964).
Oki, J. Antibiot., 42, pp. 1756–1762 (1989).

*Primary Examiner*—Michael L. Shippen
*Attorney, Agent, or Firm*—Oblon, Spivak, McClelland, Maier & Neustadt

[57] ABSTRACT

A method of killing pathogenic fungi by contacting them with an effective amount of (1R,2S)-2-aminocyclopentanecarboxylic acid (FR109615) or a salt thereof.

1 Claim, No Drawings

NEW ANTIMICROBIAL AGENT, FR109615 AND PRODUCTION THEREOF

This application is a continuation of application Ser. No. 08/258,363, filed on Jun. 10, 1994, now abandoned; which is a continuation of Ser. No. 08/133,928, filed on Oct. 12, 1993, abandoned; which is a continuation of Ser. No. 07/888,443, filed May 28, 1992, abandoned; which is a continuation of U.S. Ser. No. 07/655,996, filed on Feb. 15, 1991, abandoned; which is a continuation of Ser. No. 07/471,039, filed on Jan. 26, 1990, Now U.S. Pat. No. 5,037,809, which is a continuation of Ser. No. 07/215,339 filed Jul. 5, 1988, abandoned.

This invention relates to a new anti microbial agent, FR109615 and its salts. More particularly, it relates to a new antimicrobial composition comprising the compound, FR109615 or its salts which has an antimicrobial activity against pathogenic microorganisms, especially pathogenic fungi, and to a process for the preparation of the compound FR109615 and its salts.

According to this invention, the compound FR109615 can be prepared by culturing a FR109615 producing strain belonging to the genus Streptomyces such as *Streptomyces setonii* No. 7562 in a nutrient medium.

Particulars of microorganisms used for the production of the FR109615 and production thereof will be explained in the followings.

Microorganism

The microorganism which can be used for the production of the FR109615 is a FR109615 producing strain belonging to the genus Streptomyces, among which *Streptomyces setonii* No. 7562 has been newly isolated from a soil sample collected in Imaichi city, Tochigi Prefecture, Japan.

Lyophilized samples of the newly isolated microorganism, *Streptomyces setonii* No. 7562 have been deposited with one of the INTERNATIONAL DEPOSITORY AUTHORITY ON THE BUDAPEST TREATY, Fermentation Research Institute, Agency of Industrial Science and Technology at 1-3, Higashi 1 chome, Tsukuba-shi Ibaraki-ken 305, Japan since Jul. 1, 1987 and were assigned the deposit number FERM BP-1868 (formerly FERM P-9444).

It is to be understood that the production of the compound FR109615 is not limited to the use of the particular organism described herein, which is given for illustrative purpose only. This invention also includes the use of any mutants which are capable of producing the FR109615 including natural mutants as well as artificial mutants which can be produced from the described organism by conventional means, such as x-rays, ultra-violet radiation, treatment with N-methyl-N'-nitro-N-nitrosoguanidine, 2-aminopurine and the like.

*Streptomyces setonii* No. 7562 has the following morphological, cultural, biological and physiological characteristics.

Taxonomic studies on strain No. 7562

Strain No. 7562 was isolated from a soil sample obtained at Imaichi city, Tochigi Prefecture, Japan. The methods described by Shirling and Gottlieb[1] were employed for this taxonomic study. Morphological observations were made with light and electron microscopes from cultures grown at 30° C. for 21 days on yeast-malt extract agar, glucose asparagine agar and Bennet agar. Branching type of sporophores was monopodial and the form of mature sporophores was Rectiflexibiles with 10 to 30 spores in each chain The spores were determined by electron microscopy to be cylindrical and measured 0.4–0.6×0.8–2.2 μm in size. Spore surfaces were smooth. Neither fragmentation of hyphae nor formation of spores occurred in the substrate mycelium. Sporangia, sclerotia and zoospores were not observed.

Cultural characteristics were observed on several media described by Shirling and Gottlieb[1] and Waksman[2]. Incubation was at 30° C. for 21 days. The color names used in this study were taken from Methuen Handbook of Colour[3]. The aerial mass color belonged to white color series when grown on yeast-malt extract agar and glucose asparagine agar. Soluble pigment was not produced. Results were shown in Table 1.

Wall analysis was performed by the methods of Becker et. al.[4] and Yamaguchi[5]. Analysis of whole cell hydrolysates showed the presence of LL-diaminopimeric acid. Accordingly, the cell wall of this strain is classified as type I.

Physiological properties of strain No. 7562 were as follows. Temperature range for growth was determined on yeast-malt extract agar. Summarized physiological properties of strain No. 7562 are shown in Table 2. Temperature range for growth was from 15° C. to 34° C. with optimum temperature from 25° C. to 30° C. Gelatin liquefaction was positive. Production of melanoid pigment was negative on tyrosine agar.

Utilization of carbon was examined according to the method of Pridham and Gottlieb[6]. The results were determined after 14 days incubation at 30° C. This strain could utilize D-glucose, L-rhamnose, D-xylose, D-fructose and L-arabinose. Results were shown in Table 3.

Microscopic studies and cell wall composition of this strain belongs to the genus Streptomyces Waksman and Henrici 1943.

Accordingly, a comparison of this strain was made with published descriptions [7-11] of various Streptomyces species. Strain No. 7562 was considered to resemble *Streptomyces setonii* Waksman. Therefore, strain No. 7562 was compared with *S. setonii* IFO-13085. No significant difference was observed between the two cultures and the properties of strain No. 7562 showed good agreement with those of *S. setonii*. Therefore, strain No. 7562 was identified as a strain of *Streptomyces setonii*, and was designated as *Streptomyces setonii* No. 7562.

Literature Cited

1) Shirling, E. B. and D. Gottlieb: Methods for characterization of Streptomyces species. Intern. J. Syst. Bacteriol. 16: 313–340, 1966
2) Waksman, S. A.: The actinomycetes. Vol. 2. Classification, identification and description of genera and species. The Williams and Wilkins Co., Baltimore, 1961
3) Kornerup, A. and J. H. Wanscher: Methuen Handbook of Colour, Methuen, London, 1978
4) Becker, B., M. P. Lechevalier, R. E. Gordon and H. A. Lechevalier: Rapid differentiation between Nocardia and Streptomyces by paper chromatography of whole-cell hydrolysates. Appl. Microbiol. 12: 421–423,1964
5) Yamaguchi, T.: Comparison of the cell-wall composition of morphologically distinct actinomycetes. J. Bactriol. 89: 444–453, 1965
6) Pridham, T. G. and D. Gottlieb: The utilization of carbon compounds by some Actinomycetales as an aid for species determination. J. Bactriol. 56: 107–114,1948
7) Buchanan, R. E. and N. E. Gibbons: Bergey's manual of determinative bacteriology, 8th edition. The Williams and Wilkins Co., Baltimore, 1974
8) Shirling, E. B. and D. Gottlieb: Cooperative description of type culture of Streptomyces 2. Species descriptions from first study. Intern. J. Syst. Bacteriol. 18:69–189,1968

9) Shirling, E. B. and D. Gottlieb: Cooperative description of type culture of Streptomyces 3. Additional species descriptions from first and second studies. Intern. J Syst. Bacteriol. 18: 279–392,1968
10) Shirling, E. B. and D. Gottlieb: Cooperative description of type culture of Streptomyces 4. Species descriptions from the second, third and fourth studies. Intern. J. Syst. Bactriol. 19: 391–512,1969
11) Skerman, V. B. D., V. McGowan and P. H. A. Sneath: Approved list of bacterial names. Intern. J. Syst. Bacteriol. 30:225–420,1980

TABLE 1

Cultural characteristics of strain No. 7562

| Medium | Cultural characteristics | |
|---|---|---|
| Yeast-malt extract agar | growth | good |
| | aerial mycelium | moderate, white |
| | reverse side color | light yellow |
| | soluble pigment | none |
| Oatmeal agar | growth | poor |
| | aerial mycelium | none |
| | reverse side color | colorless |
| | soluble pigment | none |
| Inorganic salts-starch agar | growth | poor |
| | aerial mycelium | none |
| | reverse side color | colorless |
| | soluble pigment | none |
| Tyrosine agar | growth | good |
| | aerial mycelium | moderate, white |
| | reverse side color | light yellow |
| | soluble pigment | none |
| Glucose-asparagine agar | growth | good |
| | aerial mycelium | moderate, white |
| | reverse side color | pale yellow |
| | soluble pigment | none |
| Nutrient agar | growth | poor |
| | aerial mycelium | none |
| | reverse side color | colorless |
| | soluble pigment | none |
| Bennet agar | growth | good |
| | aerial mycelium | moderate, white |
| | reverse side color | pale yellow |
| | soluble pigment | none |
| Sucrose-nitrate agar | growth | poor |
| | aerial mycelium | none |
| | reverse side color | colorless |
| | soluble pigment | none |

TABLE 2

Physiological properties of strain No. 7562

| Conditions | Characteristics |
|---|---|
| Temperature range for growth | 15° C. to 34° C. |
| Optimum temperature range for growth | 25° C. to 30° C. |
| Gelatin liquefaction | positive |
| Milk coagulation | negative |
| Milk peptonization | negative |
| Starch hydrolysis | positive |
| Production of melanoid pigment | negative |
| Decomposition of cellulose | negative |

TABLE 3

Carbon utilization of strain No. 7562

| Compounds | Growth |
|---|---|
| D-glucose | + |
| Sucrose | − |
| D-xylose | + |
| D-fructose | + |

TABLE 3-continued

Carbon utilization of strain No. 7562

| Compounds | Growth |
|---|---|
| L-rhamnose | + |
| Raffinose | − |
| L-arabinose | ± |
| Inositol | − |
| Mannitol | − |

Production of FR109615

The compound, FR109615 can be produced by culturing a FR109615 producing strain belonging to the genus Streptomyces, such as *Streptomyces setonii* No. 7562 in a nutrient medium.

In general, FR109615 can be produced by culturing the FR109615 producing strain in a nutrient medium containing assimilable sources of carbon and of nitrogen, preferably under aerobic conditions (e.g. shaking culture, submerged culture, etc.).

The preferred sources of carbon in the nutrient medium are carbohydrates such as glucose, fructose, glycerin and starch. Other sources which may be included are lactose, arabinose, xylose, dextrin, molasses and the like.

The preferred sources of nitrogen are yeast extract, peptone, gluten meal, cottonseed meal, soybean meal, corn steep liquor, dried yeast, etc., as well as inorganic and organic nitrogen compounds such as ammonium salts (e.g. ammonium nitrate, ammonium sulphate, ammonium phosphate, etc.), urea, amino acid and the like.

The carbon and nitrogen sources, though advantageously employed in combination, need not be used in their pure form because less pure materials which contain traces of growth factors and considerable quantities of mineral nutrients, are also suitable for use. When desired, there may be added to medium such mineral salts as calcium carbonate, sodium or potassium phosphate, sodium or potassium iodide, magnesium salts, cobalt chloride and the like. If necessary, especially when the culture medium is foamed remarkably, a defoaming agent such as liquid paraffin, higher alcohol, plant oil, mineral oil and silicones may be added.

As conditions for the production in massive amounts, submerged aerobic cultural condition is preferred for the production of the FR109615. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the FR109615. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. As the medium, in which the vegetative inoculum is produced, there can be used the substantially same as or somewhat different medium from medium utilized for main production of the FR109615.

Agitation and aeration of the culture mixture may be accomplished in a variety of ways. Agitation may be provided by a propeller or the similar mechanical agitation equipment, by revolving or shaking the fermenter, by various pumping equipment or by the passage of sterile air through the medium. Aeration may be effected by passing sterile air through the fermentation mixture.

The fermentation is usually conducted at a temperature about between 20° C. and 40° C., preferably around 30° C., for a period of 50 hours to 100 hours, which may be varied according to the fermentation conditions and scale.

Thus produced FR109615 can be recovered from the culture medium by conventional means which are commonly used for the recovery of other fermentation products such as antibiotics.

In general, most of the FR109615 produced are found in the culture filtrate, and accordingly FR109615 can be isolated from the filtrate, which is obtained by filtering or centrifuging the broth, by a conventional method such as concentration under reduced pressure, lyophilization, extraction with a conventional solvent, pH adjustment, treatment with a conventional resin (e.g. anion or cation exchange resin, non-ionic adsorption resin), treatment with a conventional adsorbent (e.g. activated charcoal, silicic acid, silica gel, cellulose, alumina), crystallization, recrystallization and the like.

The FR109615 obtained in its free form may also be converted to its salts by treating FR109615 with an inorganic or organic acid such as hydrochloric acid, sulfuric acid, phosphoric acid, acetic acid and the like, with an inorganic or organic base such as sodium hydroxide, potassium hydroxide, ethanolamine and the like and with an amino acid such as glycine, lysine, glutamic acid and the like.

The FR109615 as obtained in the following Example has the following physicochemical properties and was assigned to the following chemical structure from the result of further studies.

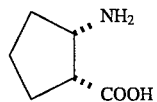

[(1R, 2S)-2-aminocyclopentanecarboxylic acid]

| Physicochemical Properties of FR109615 | | | |
|---|---|---|---|
| (1) | Appearance | Colorless prisms | |
| (2) | Molecular Weight | m/z 130 (M + H, FAB-MS) | |
| (3) | Elementary analysis | Found C 56.16, H 8.29, N 10.59% | |
| (4) | Melting point | 195–196° C. | |
| (5) | Specific rotation | $[\alpha]_D^{20} = -9.8°$ (C = 1.0, $H_2O$) | |
| (6) | UV spectrum | End absorption | |
| (7) | IR spectrum $v_{max}$ (Nujol):, | | |
| | | 2930, 2850, 2670, 2550, 2200 1640, 1610, 1560, 1545, 1530 1460, 1440, 1410, 1370, 1330 1320, 1310, 1290, 1220, 1200 1160, 1120, 1070,    1020 1000, 970, 920, 840, 780, 730 $cm^{-1}$ | |
| (8) | $^1$H-NMR Spectrum (400 MHz, $D_2O$) | | |
| | | δ 3.74 (1H, m), 2.88 (1H, m), 2.14–2.06 (2H; m), 1.87–1.70 (4H, m) ppm | |
| (9) | $^{13}$C-NMR Spectrum (67.8 MHz, $D_2O$) | | |
| | | δ 181.3(s), 53.7(d), 47.7(d), 30.0(t), 28.0(t), 21.3(t) ppm | |
| (10) | Solubility | Soluble: Water Sparingly soluble: Methanol, Ethanol Insoluble: Acetone, Ethyl acetate, Chloroform | |
| (11) | Color reaction | Positive: Ninhydrin, $KMnO_4$ Negative: Molish, Dragendorff | |
| (12) | Rf value | iso-propanol:water (75:25) | 0.46 |
| | | n-butanol:acetic acid:water (4:1:2) | 0.27 |

| Physicochemical Properties of FR109615 |
|---|
| on Silica Gel 60G Plate $F_{254}$ (Merk) |

The FR109615 has a strong antimicrobial activity against pathogenic microorganisms, especially pathogenic fungi such as pathogenic yeast (e.g. *Candida albicans*) and the like. Accordingly, the FR109615 and its pharmaceutically acceptable salt are useful as an antimicrobial agent, especially antifungal agent which is used for the treatment of infectious diseases in human beings and animals.

As examples for showing such pharmacological effects of the FR109615, some pharmacological test data are illustrated in the followings.

Test 1 (Antimicrobial activity)

Antimicrobial activity of FR109615 was measured by a conventional micro-broth dilution method using 96 well multi-trays.

A suspension of the test microorganism ($10^6$ cells/ml) was prepared by diluting an overnight cultured broth of the organism with Eagle's minimum essential medium (E. MEM). A serially diluted solution of FR109615 in E. MEM (100 μl) was added to a well of the multi-tray. To the well, the suspension of the test organism was added. The multi-trays were incubated at 37° C. for 20 hours in 5% $CO_2$ atmosphere. The obtained MIC (minimum inhibitory concentration) data are shown in the following table.

TABLE 4

| Antimicrobial activity of FR109615 | |
|---|---|
| Organisms | MIC (μg/ml) |
| Candida albicans | 16 |
| Candida krusei | 8 |
| Candida utilis | 32 |
| Mucor rouxianus | 500 |
| Tricophyton mentagrophytes | 250 |

Test 2 (Protective effect of FR109615 against fungi in experimental mice infection)

(1) Test animal

4 Weeks old mice, ICR strain, each weighing 18–21 g. One group consists of 10 mice.

(2) Test method

4 Days before challenge, the test mice intraperitoneally received a saline solution of cyclophosphamide (immunosuppressant) (200 mg). Each pf pathogenic microorganisms suspended in saline were injected into mice via the lateral tail vein. One hour after challenge, a saline solution of FR109615 was subcutaneously injected into the mice. This treatment was repeated twice a day for 2 days from the next day after challenge. Test mice were observed for survival or death for 14 days and $ED_{50}$ values were calculated by the probit method.

(3) Test result

| Microorganism | Innoculam Size(cfu/head) | $ED_{50}$ (mg/kg) |
|---|---|---|
| Candida albicans FP622 | 4.8 × $10^4$ | 0.87 |
| C. tropicalis 8001 | 5.6 × $10^4$ | 3.80 |
| C. pseudotropicalis FP584 | 2.0 × $10^7$ | 2.38 |
| C. krusei FP585 | 2.0 × $10^7$ | 0.78 |

-continued

| Microorganism | Innoculam Size(cfu/head) | $ED_{50}$ (mg/kg) |
|---|---|---|
| C. stellatoidea FP588 | $2.0 \times 10^6$ | 1.11 |

Test 3 (Protective effect of FR109615 against bacteria in experimental mice infection)

(1) Test animal

4 Weeks old mice, ICR strain, each weighing 18–21 g. One group consists of 10 mice.

(2) Test method

Pathogenic microorganism suspended in saline were injected into mice via the lateral tail vein. After challenge, a saline solution of FR109615 was subcutaneously injected into the mice (Dosage: 10 mg/kg) once a day for 4 days. Test mice were observed for survival or death for 11 days and survival ratio (%) was calculated. All of the control mice (non-treatment group) died.

(3) Test result

| Microorganism | Innoculam size (cfu) | survival ratio (%) |
|---|---|---|
| Staphylococcus aureus Smith | $2.5 \times 10^8$ | 100 |

Test 4 (Acute toxicity)

The acute toxicity of FR109615 was determined to ICR mice (female, 4 weeks old) by a single intravenous injection. No toxic symptom was observed at the dose of 1 g/kg.

A pharmaceutically acceptable salt of the FR109615 may include the salt as exemplified above.

Thus, the antimicrobial composition can be used in the form of pharmaceutical preparation, for example, in solid, semisolid or liquid form, which contains an active object compound in admixture with a pharmaceutical organic or inorganic carrier or excipient suitable for external, enteral or parenteral applications. The active ingredient may be compounded, for example, with usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, karatin, colloidal silica, potato starch, urea and other carriers suitable for use in manufacturing preparations, in solid, semisolid, or liquid form, and in addition auxiliary, stabilizing, thickening and coloring agents and perfumes. The antimicrobial compositions can also contain preserving or bacteriostatic agents thereby keeping the active ingredient in the desired preparations stable in activity. The active object compound is included in the antimicrobial composition in an amount sufficient to produce the desired therapeutic effect upon the bacterially infected process or condition.

For applying this composition to human, it is preferably to apply in a form of intravenous, intramuscular or oral administration. While the dosage or therapeutically effective amount of the FR109615 or pharmaceutically acceptable salts thereof varies from and also depends upon the age and condition of each individual patient to be treated, a daily dose of about 2–100 mg. of the active ingredient/kg. of a human being or an animal is generally given for treating diseases and an average single dose of about 50 mg., 100 mg., 250 mg. and 500 mg. is generally administered.

The following Examples are given for the purpose of illustrating this invention, but not limited thereto.

EXAMPLE 1

An aqueous seed medium (160 ml) containing 2% of corn starch, 1% of cotton-seed flour, 1% of dried yeast was poured into each of two 500 ml Erlenmeyer flasks and sterilized at 121° C. for 30 minutes. A loopful of slant culture of *Streptomyces setonii* No. 7562 was inoculated to each of the medium and cultured under shaking condition at 30° C. for 2 days.

An aqueous production medium (20 L) containing 2% of corn starch, 0.5% of cotton-seed flour, 0.5% of gluten meal, 0.25% of corn steep liquor, 0.25% of dried yeast (pH 6.8) and 0.05% of Adekanol (defoaming agent, Trademark, made by Asahi Denka Co.) was poured into a 30 L-jar fermentor and sterilized at 121° C. for 30 minutes.

The resultant seed culture broth (320 ml) was inoculated to the production medium and cultured at 30° C. for 4 days, agitated at 200 rpm and aerated at 20 liters per minutes.

The cultured broth thus obtained (20 L) was filtered with the aid of diatomaseous earth (1 kg). The filtrate (15 L) was passed through a column (60 ml) of an cation exchange resin, Diaion SK-1B ($H^+$ type, Trademark, made by Mitsubishi Chemical Industries, Ltd.). The column was washed with water (1.5 L) and eluted with 0.5N ammonium hydroxide. The eluate (4.8 L) was passed through a column (300 ml) of an anion exchange resin, Dowex 1×2 ($OH^-$ type, Trademark, made by Dow Chemical Co.). The column was washed with water (600 ml) and eluted with 0.05N acetic acid. The eluate (1.8 L) was concentrated under reduced pressure to dryness. The resultant crude powder (3 g) was applied on a column (150 ml) of Silica gel 60 (Trademark, made by Merk) and developed with 90% aqueous isopropanol. FR109615 was eluted in fractions from 630 ml to 990 ml. The active fractions were concentrated under reduced pressure to give crude crystals (1.2 g), then recrystallized from hot ethanol to give colorless crystals of FR109615 (0.8 g).

EXAMPLE 2

| FR-109615 | 5000 (g) |
|---|---|
| Sucrose | 4750 |
| Hydroxypropylcellulose | 200 |
| Starch | 50 |

The above ingredients are blended and granulated or grained in a conventional manner into granules or small granules.

We claim:

1. A method of killing pathogenic fungi comprising: contacting pathogenic fungi with an effective amount of FR109615 or a salt thereof.

* * * * *